United States Patent [19]

Vogt

[11] Patent Number: 5,454,269

[45] Date of Patent: Oct. 3, 1995

[54] DEVICE FOR COUPLING AN ULTRASONIC PROBE TO A TEST SPECIMEN BY EMPLOYING TWO-POSITION REVERSIBLE VALVES

[75] Inventor: Göran Vogt, Burgwedel, Germany

[73] Assignee: Vogt Werkstoffprufsysteme GmbH, Germany

[21] Appl. No.: 146,979

[22] Filed: Nov. 2, 1993

[51] Int. Cl.⁶ .................................................. G01N 29/28
[52] U.S. Cl. ........................................ 73/644; 310/336
[58] Field of Search .......................... 73/644, 606, 607, 73/633; 310/334, 335, 336, 328

[56] References Cited

U.S. PATENT DOCUMENTS

| 2,873,391 | 2/1959 | Schulze | 73/644 |
| 3,121,326 | 2/1964 | Klatchko | 73/644 |
| 3,958,451 | 5/1976 | Richardson | 73/644 |
| 4,563,900 | 1/1986 | Harada et al. | 73/644 |
| 4,587,849 | 5/1986 | Gross | 73/644 |

FOREIGN PATENT DOCUMENTS 0655962  4/1979  U.S.S.R. .................................. 73/644

2036321  6/1980  United Kingdom ..................... 73/644

Primary Examiner—Hezron E. Williams
Assistant Examiner—Nashmiya Ashraf
Attorney, Agent, or Firm—Banner & Allegretti, Ltd.

[57] ABSTRACT

A method for coupling an ultrasonic probe to a test specimen, whereby a cushion of fluid is formed between the two bodies to facilitate the coupling. In order to optimize the coupling, reduce the quantity of coupling fluid as well as prevent a drain off of the coupling fluid, a vacuum is produced during the attachment of the probe to the test specimen at the end of the probe facing the surface of the test specimen. Coupling fluid is drawn by the vacuum into the gap between the probe and the specimen to form a fluid cushion. The device for coupling the probe to the test specimen is equipped with a guiding and retaining housing for the probe through which the fluid may be supplied to the gap between the two bodies in order to form the cushion of fluid. The gap between the two bodies is connected through channels in the housing to a vacuum source and a container for the coupling fluid.

7 Claims, 1 Drawing Sheet

DEVICE FOR COUPLING AN ULTRASONIC PROBE TO A TEST SPECIMEN BY EMPLOYING TWO-POSITION REVERSIBLE VALVES

BACKGROUND OF THE INVENTION

The invention pertains to a method and a device for coupling a first body to a second body, in particular for coupling an ultrasonic probe to test specimens, by means of a cushion of fluid.

Coupling ultrasonic probes to test specimens via intermediate layers, water gap coupling, and submersion technology is known from prior art. However, intermediate layers increase the interference echoes if impulse echo technology is used. The water gap coupling or submersion technology is thus primarily utilized for mechanized testing of large quantities of identical test specimens. In both, process water is supplied under pressure. The quantity of water used is very high, and the probe must be pressed against the test specimen (as described in "*Werkstoffprüfung mit Ultrascha*" ("Materials Testing with Ultrasound") by Krautkrämer, Springer Publishing House, Berlin, Heidelberg, New York, London, Paris, Tokyo, 1986, pp. 300–305).

THE INVENTION

The object of this invention is to provide a method and a device of this type in which the coupling is optimized, smaller quantities of coupling fluid are required, a drain off of coupling fluid is prevented, and the disadvantages of known processes are eliminated.

According to the invention, the coupling fluid is not directed into the coupling gap under super atmospheric pressure, but from an annular space surrounding the gap by means of a vacuum. The probe is automatically drawn against the test specimen by the vacuum so it is not necessary to press the probe by external means against the test specimen. The coupling fluid is recirculated, so that the consumption of coupling fluid is very low. With the construction according to the invention, the continuous fluid flow is automatically interrupted when the probe is removed from the test specimen, since the vacuum is broken once the probe has been lifted from specimen surface. The coupling fluid automatically begins to flow and circulate again once the probe is reattached to the surface of the specimen since the vacuum is immediately reestablished on contact. The annoying process of turning a pump on and off is thus no longer required.

Although the utilization of a vacuum builds up the desired cushion of fluid between the ultrasonic probe and the test specimen, the suction produced ensures that no fluid drains off from the surface of the test specimen.

THE DRAWINGS

The invention is described in detail below with the aid of the enclosed figures which illustrate a preferred operative example.

In the drawings:

FIG. 1 is a schematic sectional representation of a device according to the invention for coupling an ultrasonic probe to a test specimen, and FIG. 2 is a schematic representation illustrating the function of the device according to FIG. 1 when connected to vacuum and liquid sources.

DETAILED DESCRIPTION

Figure 1:
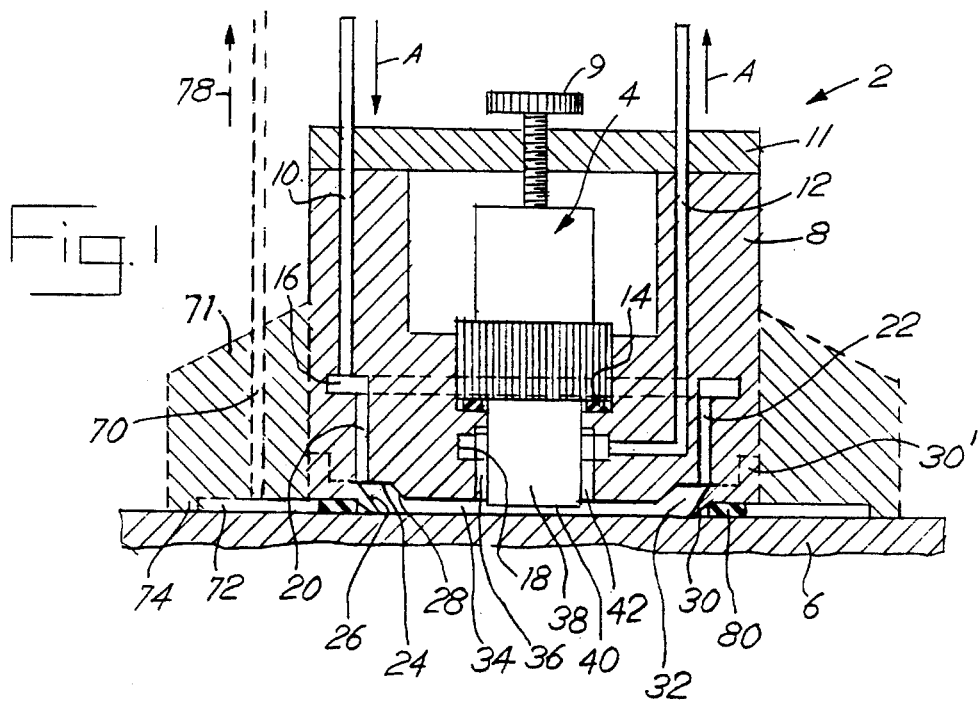

Identical structural components are marked in the figures with identical reference numerals.

The figures show a device 2 for coupling an ultrasonic probe 4 to a test specimen 6.

The cylindrical probe 4 is mounted in a central opening in an annular probe-retaining device or housing 8 and axially positioned via an adjusting screw 9 arranged in a plate 11 covering the open end of housing 8. The probe 4 is provided in the illustrated application example with a coupling body 38 which, for example, consists of plexiglass. The probe is pressed against an elastic seal 14 seated on a shoulder within the opening in the housing. Two conduits 10 and 12 for the supply or discharge of water or other coupling fluid are machined into the housing 8.

A flat annular space 16 is provided inside of the housing 8, and connects to axially-disposed channels 20, 22 machined into the inner surface of said annular space surrounding coupling body 38 of probe 4, and radially spaced therefrom.

The conduit 10 exits into the annular space 16. The other conduit 12 exits into another annular groove or recess 18, adjacent the wall of coupling body 38. At least two channels 20 and 22 are circumferentially arranged in the housing 8, which channels connect the annular space 16 to an annular groove 32 cut in the lower face of the housing opposite the surface of the test specimen. Groove 32 has side walls 26, 28 which incline radially towards the probe. The outer wall of the annular groove 32 has an annular extension or lip 30 serving as a probe guide and seal for attachment of the probe to the test specimen 6. The lip comprises part of a ring 30' which is a separate part attached to the housing. Thus the annular inclined groove 32, a flat annular chamber 34, and an axial central opening 36 are formed at the surface of the test specimen when the test specimen 6 is attached to the housing 8. The coupling body 38 projects into the central opening 36, so that an annular axial space or ring chamber 42 is formed around the coupling body of probe 4. The lip 30 may extend transversely towards the inside as an extension of the outer wall of the annular groove 32 as illustrated in the figures, or simply protrude perpendicularly, even at a distance from the outer wall. The lip 30 may also be constructed integrally with the housing rather than as a separate attachable ring 30' as indicated in FIG. 1.

The coupling body 38 of the probe protrudes beyond the lower face of the housing 8 by a smaller distance than the annular lip 30 so that a narrow gap 40 remains when the housing is in contact with the surface of the test specimen.

The conduit 12 connects to the annular recess 18 and thus into the ring chamber 42.

The coupling body 38 may also be omitted, in which case, the lower end of the probe 4 projects through the central opening 36 to the same extent.

A two-position reversible valve 46 is connected via lines 48 and 50 to the conduits 12 and 10, respectively. The directional control valve connects the conduits 10 and 12 with either of two ascending tubes 52 and 54 communicating with tanks 56 and 58 for the coupling fluid.

An additional two-position reversible valve 60 connects two additional lines 62 and 64, which extend into the upper portion of the tanks 56 and 58, with a vacuum source 66.

Figure 2:
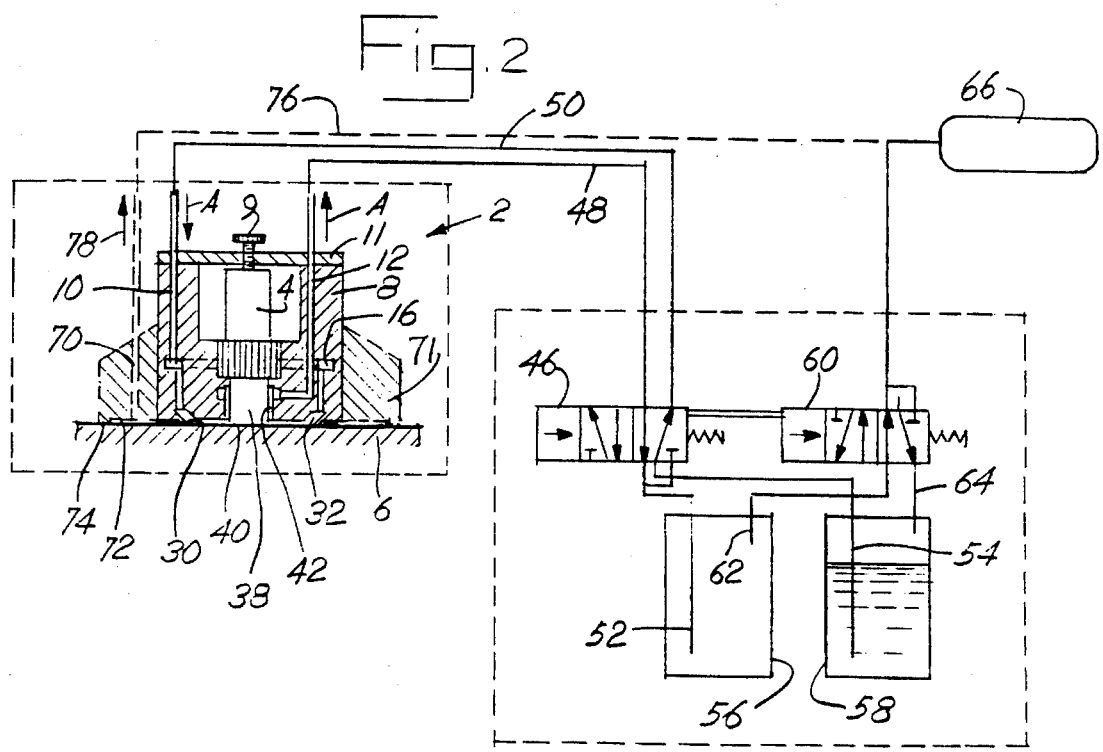

A collar 71 may be provided around housing 8, which collar contains a channel 70 which connects to an annular chamber 72 surrounding the lip 30. The annular chamber 72 is formed by providing an annular axial projection 74 outside of the lip 30, which projection extends below the bottom of housing 8 to the identical extent as the probe lip 30. The vacuum source 66 is connected via a line 76 to channel 70 in order to produce the vacuum in the annular chamber 72. The direction of suction is indicated in FIG. 2 by the arrow 78.

Filters (not shown) may be arranged in the connecting lines 48 and 50.

The device illustrated in the figures operates as follows:

The tank 58 is filled with water up to a predetermined level below the end of line 64, and its ascending tube 54 is connected via the directional control valve 46 and the line 50 to the conduit 10 which in turn communicates with the annular recess 18, the channels 20, 22, and the annular groove 32. The ascending tube 52 of the tank 56 is connected via the directional control valve 46 and the line 48 to the conduit 12 and thus also to the annular recess 18 and the ring chamber 42. The line 62 in the tank 56 is connected via the directional control valve 60 to the vacuum source 66, while the line 64 in the container 58 is open to the atmosphere.

Assume the vacuum source is in its operating mode. Valve 60 is open between the vacuum tank 66 and empty tank 56, to reduce the pressure in tank 56. Valve 46 is open to tank 56 and line 48 which connects to conduit 12 in housing 8. If the probe 2 is now attached to the test specimen 6, a vacuum is built up in the annular recess 18 and in the ring chamber 42 via the conduit 12, and line 48 which is connected to tank 56 through valve 46 and line 52. The aforementioned vacuum in ring chamber 42 causes fluid to be drawn from tank 58 to housing 8 through the ascending tube 54, the directional control valve 46, line 50 and conduit 10. Thus, cushioning fluid fills narrow gap 40 as it flows from groove 32 and chamber 34. Fluid exits from device 2 through ring chamber 42, channel 12, line 48 directional control valve 46, and ascending tube 52 into tank 56. The flow direction of the coupling fluid in the lines 48 and 50 is indicated by arrows A above the probe.

As soon as the water level in the tank 58 has been sufficiently lowered, the valves 46 and 60 are reversed, so that the upper space of the tank 58 is now connected to the vacuum source 66 via the line 64, and the line 62 extending into the tank 56 is open to the atmosphere. The function of the tanks is now reversed, which means that the water is transported from the tank 56 through the device 2 into container 58. The flow direction through the probe retaining device is not changed.

The flow direction through the housing 8 may be reversed if the line 48 is connected to the channel 10, and the line 50 is connected to the channel 12, all of which represents a different arrangement than the one illustrated in FIG. 2. Water flows either out of the ring chamber 42 towards the annular groove 32 or vice versa by producing a vacuum either in the annular groove 32 or in the ring chamber 42 after the attachment of the probe housing 8 to the test specimen 6. In either case, the space between the probe and the surface of the test specimen, in other words the gap space 40, is filled with coupling fluid. Thus, the cushion of fluid required for the coupling process is formed in this fashion between the bottom of the probe and the surface of the test specimen.

An additional vacuum may be produced in the chamber 72 via the lines 76 and the channel 70, which vacuum serves the purpose of preventing the introduction of air and air bubbles into the chambers 32, 34, and 42 and thus into the circuit within housing 8. The vacuum in the enclosed space 72 additionally causes the device 2 with the probe 4 to be drawn and retained against the surface of the test specimen. The force produced by the vacuum additionally contributes to seal the annular groove 32 from the outside.

The probe housing may be additionally provided on the side facing the test specimen with an annular seal or gasket 80 which may also be constructed as part of the attached ring seal 30'. The gasket 80 may be arranged either outside or inside of the lip 30.

If the test specimen consists of a ferromagnetic material, the retaining function may also be attained by a magnet which is connected to the probe housing.

The width selected for the gap 40 is preferably so narrow that a capillary effect is created. The capillary effect serves the important function of preventing air bubbles from penetrating into the gap 40 due to currents.

I claim:

1. In combination, an ultrasonic probe having a sensing surface and a test specimen slightly spaced from the sensing surface of said probe to provide a gap therebetween for holding a liquid coupling cushion comprising a cylindrical housing surrounding said probe and having a peripheral seal in sealing engagement with said test specimen to seal said gap from the atmosphere, a first and a second conduit within said housing, each communicating with said gap, a first tank for coupling liquid connected to said first conduit, a second tank for coupling liquid connected to said second conduit, a source of vacuum connecting to said first tank and to said second tank, and two position reversible valve means between said tanks and said conduits and between said tanks and said vacuum source, whereby, with said valve means in a first position, coupling liquid is drawn from said first tank, through said housing conduits and said gap and into said second tank by means of vacuum drawn on said second tank and, with said valve means in a second position, coupling liquid is drawn from said second tank through said housing conduits and said gap and into said first tank by means of vacuum drawn on said first tank.

2. The combination of claim 1 in which said first conduit communicates with said gap by means of a flat annular chamber inside said peripheral seal and surrounding said gap between said housing and said test specimen and said second conduit communicates with said gap by means of a ring chamber surrounding said probe which ring chamber connects to said annular chamber.

3. The combination of claim 2 in which said housing has a surface facing said test specimen which surface includes an annular groove disposed between the periphery of said flat annular chamber and said peripheral seal.

4. The combination of claim 3 in which said probe has an axial wall and said housing has a plurality of axially-extending channels radially spaced from said axial wall, opening into said annular groove, and connecting to said first conduit.

5. The combination of claim 3 in which said peripheral seal is formed as a lip extending radially inward toward said probe.

6. The combination of claim 3 in which said peripheral seal is a separate part attached to said housing.

7. The combination of claim 3 which includes a collar surrounding said housing, said collar having an axial projection in contact with said test specimen to enclose a space surrounding said peripheral seal, and means for connecting said enclosed space to a vacuum source.

* * * * *